(12) United States Patent
Honda et al.

(10) Patent No.: US 6,651,382 B1
(45) Date of Patent: Nov. 25, 2003

(54) METHOD FOR PREVENTING THE RELEASE OF GRAMINEOUS PLANT POLLENS

(75) Inventors: Ichiro Honda, Ibaraki (JP); Michihiro Wada, Ibaraki (JP); Tokuhiko Makino, Ibaraki (JP)

(73) Assignee: National Agricultural Research Organization (JP)

( * ) Notice: Subject to any disclaimer, the term of this patent is extended or adjusted under 35 U.S.C. 154(b) by 0 days.

(21) Appl. No.: 09/679,551

(22) Filed: Oct. 6, 2000

(30) Foreign Application Priority Data

Oct. 8, 1999 (JP) ............................................ 11-288173

(51) Int. Cl.⁷ ........................ A01B 79/00; A01B 79/02; A01C 1/00; A01G 1/00; A01H 3/00; A01N 25/00
(52) U.S. Cl. ..................................... 47/58.1; 504/116.1
(58) Field of Search ..................... 47/58.1 R; 504/116.1

(56) References Cited

FOREIGN PATENT DOCUMENTS

| DE | 209379 | | 5/1984 |
| DE | 218826 | A1 | 2/1985 |
| DE | 221059 | A1 | 4/1985 |
| JP | 07267802 | A | 10/1995 |
| JP | 11139907 | A | 5/1999 |
| JP | 11139908 | A | 5/1999 |
| JP | 11255601 | A | 9/1999 |
| WO | WO 94/18833 | | 9/1994 |
| WO | WO 96/06529 | | 3/1996 |
| WO | WO 99/24388 | | 5/1999 |

OTHER PUBLICATIONS

Lee et al., Physiological and Biochemical Changes Related to Methyl Jasmonate–Induced Chilling Tolerance of Rice (*Oryza Sativa* L.) Seedlings; Plant, Cell and Environment; vol. 19, No. 1, Abstract, 1996.*
Dathe, Effects of Jasmonic Acid and Ethephon on Tillering to Maturity in Spring Barley; Annals of Botany; 69(3), pp. 237–241, 1992.*
Zeng et al.; Opening of Rice Floret in Rapid Response to Methyl Jasmonate; Journal of Plant Growth Regulation; vol. 18, No. 4, pp. 153–158; 1999.*
Anthony Huxley; The New Royal Horticultural Society Dictionary of Gardening; 1992; p. XLV.*
Soukhanov, A. et al.; Webster's II New Riverside University Dictionary; The Riverside Publishing Company; 1994; p. 413.*

* cited by examiner

*Primary Examiner*—Kent Bell
(74) *Attorney, Agent, or Firm*—Finnegan, Henderson, Farabow, Garrett & Dunner, L.L.P.

(57) ABSTRACT

The object of the present invention is to develop a technique for preventing the release of pollens in order to keep varieties from hybridizing. It has become clear that the application of jasmonic acid derivatives to the ear of a gramineous plant before the time of flowering inhibits the bloom and prevents the release of pollens.

2 Claims, No Drawings

METHOD FOR PREVENTING THE RELEASE OF GRAMINEOUS PLANT POLLENS

FIELD OF THE INVENTION

The present invention relates to a method for changing the flowering characteristics of plants, preventing the release of pollens due to flowering and keeping varieties from hybridizing.

BACKGROUND OF THE INVENTION

Gramineous plants are monoclinous and go to seed by self-pollination. Generally, gramineous plants are characterized in that, at the time of flowering, the anthers protrude from the flower and release pollens in the air. For this reason, it is known that the pollens may cover affinous plant varieties reseeding in the neighborhood, and may hybridize with them depending on the varieties.

It is known that there are some specific mutants which neither come into flower nor release pollens among gramineous plants, and that even flowering varieties sometimes pollinate without coming into flower depending on the environment. However, a method of controlling the flowering of flowering varieties is still unknown.

On the other hand, plants having a herbicide-resistant gene are being produced through gene recombination techniques. Herbicide-resistant plants are generated so that they have resistance to herbicide, when other plants are controlled by the herbicide. However, it is pointed out that, since the herbicide-resistant plants hybridize with wild varieties reseeding in the neighborhood through the release of pollens at the time of flowering, wild varieties also obtain resistance and accordingly it becomes difficult to control them with the herbicide. For this reason also, the establishment of a technique for preventing the release of pollens is required.

SUMMARY OF THE INVENTION

The object of the present invention is to develop a technique for preventing the release of pollens in order to keep varieties from hybridizing.

As a result of the present inventors' thorough work directed to achieve the above object, it has become clear that the application of jasmonic acid derivatives to the ears of gramineous plant before the time of flowering inhibits the bloom and prevents the release of pollens.

DETAILED DESCRIPTION OF THE INVENTION

The present invention relates to:

(1) a method for preventing the release of pollens, which comprises treating gramineous plants with jasmonic acid derivatives, (2) an agent for preventing the release of gramineous plant pollens, which comprises jasmonic acid derivatives.

The jasmonic herein include all compounds which are considered to have the activity of jasmonic acid, regardless of whether they are natural or synthetic. That is, examples of jasmonic acids do not only include the natural type of (−)-jasmonic acid and (−)-methyl jasmonate, but also racemic mixtures thereof, i.e., (±)-jasmonic acid and (±)-methyl jasmonate, and related compounds such as tuberonic acid, epijasmonic acid, cucurbic acid and so on.

The gramineous plants used herein include bristle grass (*Setaria viridis*), zoysia, *Sorghum halepense* and foxtail (*Alopecurus myosuroides*) as well as rice, winter cereals such as barley or wheat, foxtail millet, Japanese millet and so on.

As a method of treatment, it is preferable to spray the agent on the ears in aqueous solution form before the time of flowering. Accordingly, it is also possible to dissolve a tablet containing jasmonic acid derivatives in water and use it as aqueous solution.

The present invention is further described in the following example. The example is provided for illustrative purposes only, and is not intended to limit the scope of the invention.

EXAMPLE

A flowering barley line derived from a barley line "Satsuki-Nijo" was conventionally cultivated in the fields. At the earing time, unflowered ears immediately after earing were harvested. Each group of three ears was then treated with 10 cc reagent solution containing 1–100 ppm methyl jasmonate as a jasmonic acid derivative in an artificial climate chamber under the following conditions: in the light having a brightness of 120 $\mu$mol photons/cm$^2$ for 14 hours at 25° C.; and in the dark for 10 hours at 15° C.

While optionally supplying water consumed by the ears, their flowering condition was observed for 6 days. Flowered ears were transferred to a culture medium for cuttings and cultivated for about 20 days. The number of anthers remaining in a glumaceous flower after self-pollination was measured and used as a control. The results are shown in Table 1.

TABLE 1

| Treating reagent | Reagent concentration (ppm) | Number of flowered ears on the 6th day | Number of remaining anthers per one glumaceous flower |
|---|---|---|---|
| Methyl jasmonate | 1 | 3 | 0.7 |
| Methyl jasmonate | 10 | 3 | 1.7 |
| Methyl jasmonate | 100 | 0 | 2.1 |
| Non-treated |  | 3 | 0.9 |

As shown in Table 1, no flowering was observed in the ears treated with 100 ppm methyl jasmonate, indicating that the treated ears are inhibited from flowering when compared with non-treated ears. Regarding the number of remaining anthers per one glumaceous flower, the ears treated with 10 ppm methyl jasmonate apparently have more anthers than non-treated ears, indicating that the treated ears are inhibited from flowering. The ears treated with 100 ppm methyl jasmonate have many more remaining anthers, indicating that the treated ears are further inhibited from flowering.

The same test as described above was repeated again, and similar results were obtained, as shown in Table 2.

TABLE 2

| Treating reagent | Reagent concentration (ppm) | Number of flowered ears on the 6th day | Number of remaining anthers per one glumaceous flower |
|---|---|---|---|
| Methyl jasmonate | 1 | 3 | 1.1 |
| Methyl jasmonate | 10 | 3 | 1.7 |
| Methyl jasmonate | 100 | 0 | 2.6 |
| Non-treated |  | 3 | 1.0 |

Accordingly, these results show that it is desirable to spray 10 ppm or more jasmonic acid derivatives to inhibit the flowering of gratnineous plants.

Treatment with jasmonic acid derivatives inhibits the flowering of gramineous plants, thereby preventing the release of their pollens. Thus, this treatment can prevent the hybridization between varieties and stop the growth and spread of weeds.

What is claimed is:

1. A method for controlling the release of pollens from barley, comprising the step of administering jasmonic acid derivative to the unopened flowers on ears of the barley plants so as to control the release of pollens.

2. A method for inhibiting flower opening in barley, comprising the step of administering a jasmonic acid derivative to the unopened flowers on ears of the barley plants so as to inhibit flower opening.

* * * * *